(12) United States Patent
White

(10) Patent No.: US 6,273,338 B1
(45) Date of Patent: Aug. 14, 2001

(54) LOW COST COLOR-PROGRAMMABLE FOCUSING RING LIGHT

(76) Inventor: Timothy White, 146 Lull Rd., New Boston, NH (US) 03070

(*) Notice: Subject to any disclaimer, the term of this patent is extended or adjusted under 35 U.S.C. 154(b) by 0 days.

(21) Appl. No.: 09/158,735

(22) Filed: Sep. 22, 1998

(51) Int. Cl.[7] .................................................... G06K 7/10
(52) U.S. Cl. ........................................ 235/462.42; 235/455
(58) Field of Search .............................. 235/455, 462.01, 235/462.1, 462.06, 462.11, 462.24, 462.36, 462.29, 472.01, 462.41, 462.42

(56) References Cited

U.S. PATENT DOCUMENTS

| | | |
|---|---|---|
| 2,792,740 | 5/1957 | Haynes . |
| 2,926,559 | 3/1960 | Oppenheimer . |
| 2,934,601 | 4/1960 | Oppenheimer . |
| 3,322,487 | 5/1967 | Renner . |
| 3,558,894 | 1/1971 | LaRosiaz et al. . |
| 3,596,083 | 7/1971 | Lovering . |
| 3,944,336 | 3/1976 | Carr . |
| 3,984,157 | 10/1976 | LeVantine . |
| 3,985,425 | 10/1976 | Clapp . |
| 4,067,026 | 1/1978 | Pappanikolaou . |
| 4,139,306 | 2/1979 | Norton . |
| 4,185,902 | 1/1980 | Plaot . |
| 4,341,449 | 7/1982 | Iwata . |
| 4,555,635 | 11/1985 | Yoshida . |
| 4,561,722 | 12/1985 | Smetana . |
| 4,601,576 | 7/1986 | Galbraith . |
| 4,677,473 | 6/1987 | Okamoto . |
| 4,691,231 | 9/1987 | Fitzmorris et al. . |
| 4,712,889 | 12/1987 | Schindl . |
| 4,735,497 | 4/1988 | Elterman . |
| 4,791,534 | 12/1988 | Lindberg . |
| 4,816,686 | 3/1989 | Hara et al. . |
| 4,854,688 | 8/1989 | Hayford et al. . |
| 4,877,326 | 10/1989 | Chadwick et al. . |
| 4,882,498 | 11/1989 | Cochran et al. . |
| 4,965,665 | 10/1990 | Amir . |
| 4,972,093 | 11/1990 | Cochran et al. . |
| 4,991,947 | 2/1991 | Sander et al. . |
| 5,011,265 | 4/1991 | Tamamura et al. . |
| 5,039,868 | 8/1991 | Kobayashi et al. . |
| 5,051,825 | 9/1991 | Cochran et al. . |
| 5,060,065 | 10/1991 | Wasserman . |
| 5,064,291 | 11/1991 | Reiser . |
| 5,072,127 | 12/1991 | Cochran et al. . |
| 5,104,210 | 4/1992 | Tokas . |
| 5,155,558 | 10/1992 | Tannenbaum et al. . |

(List continued on next page.)

Primary Examiner—Thien M. Le

(57) ABSTRACT

Provided herein are devices and methods of illuminating an object. The devices may include a housing having an inner reflective surface, an illumination source, disposed in a ring on the inner reflective surface of the housing, a fresnel lens disposed on the housing opposite the inner reflective surface, for focusing illumination to the object, and a partially reflective reflector, disposed on the fresnel lens, for transmitting illumination to the object and for reflecting illumination to the inner reflective surface. The illumination source may be a plurality of plurality of light emitting diodes disposed in a ring about the inner reflective surface, a ring light, or other illumination source. The partially reflective reflector may be a half-silvered mirror. The devices may further include a camera for viewing the object, an image processor, for processing an image from the camera, and a processor, for storing, manipulating and retrieving data corresponding to the image. The processor may be part of a system for inventory, materials handling, process control, or the like, or may be part of a machine vision device, such as a matrix code reader or a hand held scanner. The fresnel lens may be made interchangeable, so that lenses of different focal lengths may be used for viewing objects at different distances from the device. The device may include a circuit for controlling at least one of the color and the intensity of the illumination source.

34 Claims, 7 Drawing Sheets

U.S. PATENT DOCUMENTS

| | | |
|---|---|---|
| 5,172,005 | 12/1992 | Cochran et al. . |
| 5,187,611 | 2/1993 | White et al. . |
| 5,461,417 | 10/1995 | White et al. . |
| 5,539,485 | 7/1996 | White . |
| 5,604,550 | 2/1997 | White . |
| 5,684,530 | 11/1997 | White . |
| 5,713,661 | 2/1998 | White . |
| 5,761,540 | 6/1998 | White . |
| 5,764,874 | 6/1998 | White . |

LOW COST COLOR-PROGRAMMABLE FOCUSING RING LIGHT

FIELD OF THE INVENTION

The invention pertains to the field of illumination, and in particular to methods and systems for providing a large solid angle of high intensity illumination of an observed object.

DESCRIPTION OF THE RELATED ART

Electronic machine vision apparatuses are commonly employed in conjunction with automatic manufacturing, machining, assembly and inspection apparatuses, particularly of the robotics type. Observing apparatuses, such as television cameras, are commonly employed to observe the object being machined, assembled, or inspected, and the image received and signal transmitted by the camera can be compared to a standard image or signal stored in a database to determine if the observed article is properly machined, oriented, or assembled. Also, machine vision is widely used in inspection and flaw detection applications whereby inconsistencies and imperfection in both hard and soft goods can be rapidly ascertained and adjustments or rejections instantaneously effected.

When the object being observed has a shiny specular surface, reflections of non-uniformities in the local lighting environment may create misleading visual features that interfere with the accuracy of the inspection task such as the appearance of a reflected shadow on a laser etched letter "I" causing it to appear to the machine vision apparatus as the letter "T". In the inspection of soldered circuits such as those used with printed circuit boards, the highly reflective nature and uneven surface geometry of the solder makes it very difficult to obtain an accurate electronic signal, and the same is true when machine vision is used to inspect laser etched metal surfaces, reflective packaging, and other objects having shiny surfaces, particularly irregular shiny surfaces.

In order to view a mark, image contrast is necessary between the mark and the underlying material. Specular surfaces require a specific illumination geometry to achieve the required image contrast for the features of interest, which is determined by the angle of viewing and the surface's geometry relative to the optical axis between the surface and the viewer. For normal viewing of a flat specular surface, i.e., a surface in which the optical axis is perpendicular to the surface being imaged and the surface is substantially a plane, the light source must have a width equal to at least twice the size of the object field of view plus the diameter of the camera aperture for a normal lens if the light source is integrated with the camera. This relationship is independent of distance from the light source to the surface being observed.

Uneven specular surfaces require a large solid angle of uniform illumination to appear uniformly illuminated, depending on the degree of surface unevenness. A large solid angle of illumination is characterized by light striking the surface to be viewed over a large continuous range of incident angles. A solid angle of front illumination of 160° allows a specular surface with approximately +/−40° of unevenness to appear uniformly illuminated.

Illumination systems exist that produce illumination that is continuous and uniform in nature and is free of dark, bright or void portions capable of generating erroneous vision signals. Examples of such systems are disclosed in U.S. Pat. Nos. 5,684,530 and 5,461,417, each of which discloses a continuous diffuse illumination ("CDI") method and apparatus. The disclosure of each of such U.S. Patents is incorporated by reference herein. CDI illumination provides dramatically improved results when machine vision is used to view shiny, irregular objects.

FIGS. 1–6 depict various illumination geometries that have been traditionally used in machine vision systems along with their associated incident angle brightness histograms. For example, in FIG. 1, a coaxial illumination system 1 is employed to illuminate an object 2 as it is viewed by an electronic machine vision camera 3. As can be seen from the incident angle brightness histogram shown in FIG. 2, this coaxial illumination system provides a uniform extended illumination zone 4 with a desirable incident illumination level that coincides with a zero angle of incidence off of the observation axis but is substantially devoid of any illumination as the angle of incidence deviates from zero.

FIG. 3 depicts an off-illumination axis diffuse dome lighting system 5 illuminating an object 2 to be observed by electronic machine vision camera 3 through an observation window 6, which can be an opening or orifice or even a zone of material that appears transparent to a machine vision camera, such as clear plastic or the like. This illumination system creates the uniform diffuse illumination zone 4 shown in FIG. 4. While the incident illumination level is substantially uniform as the angle of incidence of the light increases away from a zero angle of incidence off of the observation axis, the on-observation axis region 7, which has an angle of incidence approaching zero degrees off-axis, is substantially devoid of any illumination.

A conventional ring illumination system and its corresponding incident angle brightness histogram, as depicted in FIGS. 5 and 6 respectively, provides a uniform diffuse illumination zone 4 with a substantially uniform incident illumination level that corresponds to substantially the same shape as the ring illuminator 8 being employed.

FIGS. 7, 8, 9, and 10 show four illumination systems and methods and their respective incident angle brightness histograms. First, FIG. 7 shows a continuous diffuse illumination system that is comprised of a combination of the coaxial illumination system 1 of FIG. 1 and the off-illumination axis diffuse illumination system 5 of FIG. 3. The combination of these two illumination components results in a lighting environment with the incident angle brightness histogram shown in FIG. 8. This environment is characterized by a diffuse illumination zone 4 with a substantially uniform incident illumination level irrespective of the angle of incidence.

When utilizing machine vision techniques, it is common to employ complicated fighting systems for illumination the object being observed. Some such systems eliminate shadows, highlights, reflections and other lighting characteristics caused by shiny convex surface objects. Other systems provide increased contrast to images printed on dull, flat surfaces. Examples of complex lighting systems for use with machine vision apparatus are shown in U.S. Pat. Nos. 4,677,473; 4,882,498; 5,051,825; 5,060,065 and 5,072,127. The disclosure of such patents is incorporated by reference herein. The devices shown in these patents are capable of generating improved lighting characteristics. However, such devices may in some instances be too complex or expensive to manufacture relative to the benefit they provide. Also, some devices may require a relatively intense, illumination source. Accordingly, a simple to manufacture device that provides adequate illumination of uneven specular surfaces at high-efficiency is desirable.

FIGS. 11 and 12 depict a side view and a bottom view, respectively, of a fresnel lens 12. A conventional fresnel lens includes a series of concentric grooves 12, shaped onto a flat, thin piece of material. A fresnel lens may be formed from a variety of light transmitting materials through conventional manufacturing techniques. For example, it may be molded from plastic or acrylic. The fresnel lens 10 may be used to replace the curved surface of a conventional lens. The concentric grooves 12 act as refracting surfaces, bending parallel rays to a common focus. Different fresnel lenses may have concentric grooves of different angles, so that lenses of a variety of focal lengths may be provided.

SUMMARY OF THE INVENTION

Provided herein is a low-cost high-efficiency illumination method and apparatus, which may be a method and apparatus for illuminating an object, wherein illumination of the object is by an illumination source, a partially reflective reflector, a reflecting cavity, and a fresnel lens. The methods and apparatuses may include an electronic machine vision camera for receiving an image of an object and transmitting data corresponding to the image, an image processor, for receiving the data from the camera and generating data corresponding to the signal and a computer, for receiving, storing, manipulating and retrieving data from the image processor.

Provided herein are devices and methods of illuminating an object. The devices may include a housing having an inner reflective surface, an illumination source disposed in a ring on the inner reflective surface of the housing, a fresnel lens disposed on the housing opposite the inner reflective surface, for focusing illumination to the object, and a partially reflective reflector, disposed on the fresnel lens, for transmitting illumination to the object and for reflecting illumination to the inner reflective surface. The illumination source may be a plurality of light emitting diodes disposed in a ring about the inner reflective surface, a ring light, or other illumination source. The partially reflective reflector may be a half-silvered mirror. The devices may further include a camera for viewing the object, an image processor, for processing an image from the camera, and a processor, for storing, manipulating and retrieving data corresponding to the image. The processor may be part of a system for inventory management, materials handling, process control, or the like, or may be part of a machine vision device, such as a matrix code reader, robotic arm or hand held scanner. The fresnel lens may be made interchangeable, so that lenses of different focal lengths may be used for viewing objects at different distances from the device. The device may include a circuit for controlling at least one of the color and the intensity of the illumination source.

The practice of the concepts of the invention may be utilized in machine vision applications with objects having specular surfaces, including machined or molded surfaces of convex or concave configurations and surfaces containing numerous convex and concave texture elements such as those found in materials such as embossed metal foil, matte-finish photographs and the like. However, it will be appreciated that the inventive concepts disclosed herein are also applicable to film camera, video camera, digital camera and microscope-aided human inspection systems, to line-scanning image sensors and photocopiers, and to other applications where proper illumination is required in order to obtain acceptable image quality.

As will be appreciated from the following description, the apparatus permitting the practice of the invention is relatively simple and inexpensive as compared with prior art devices for providing continuous diffused illumination conditions.

BRIEF DESCRIPTION OF THE DRAWINGS

The aforementioned objects and advantages of the invention will be appreciated from the following description and accompanying drawings wherein.

DETAILED DESCRIPTION OF THE INVENTION

Figure 1:
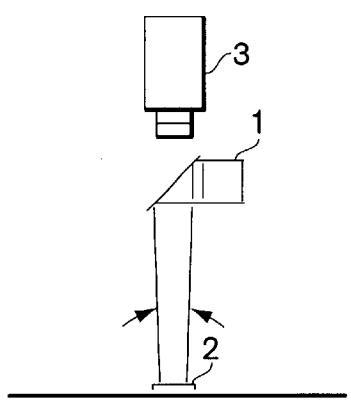
FIGS. 1,3 and 5 depict traditional illumination geometries used in conjunction with machine vision systems, namely coaxial illumination, off-axis diffuse illumination, and ring illumination respectively.
Figure 2:
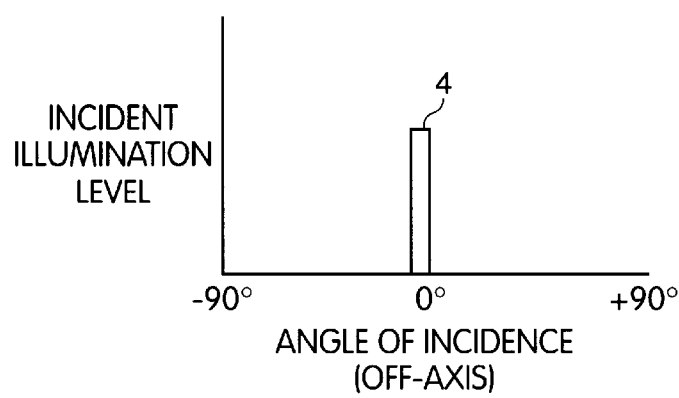
FIGS. 2,4 and 6 depict incident angle brightness histograms, which are graphs plotting incident illumination level a function of angle of incidence, associated with the lighting geometries depicted in FIGS. 1, 3 and 5 respectively.
Figure 3:
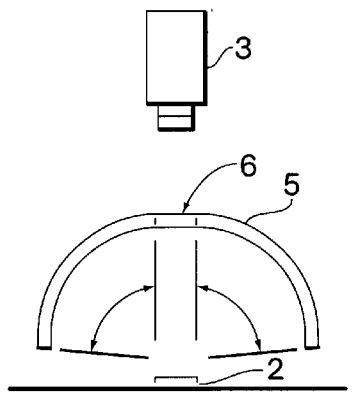
Figure 4:
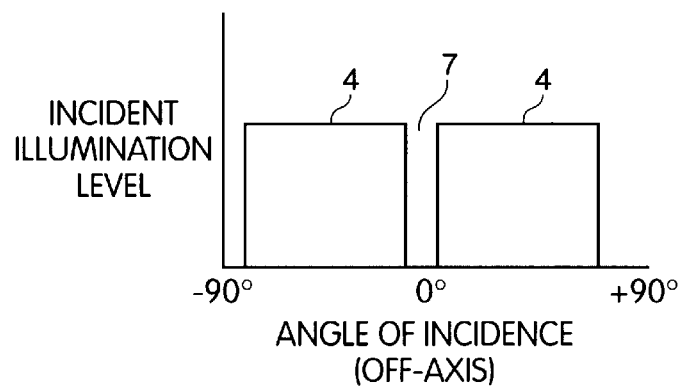
Figure 5:
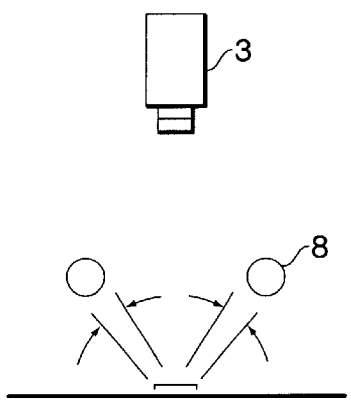
Figure 6:
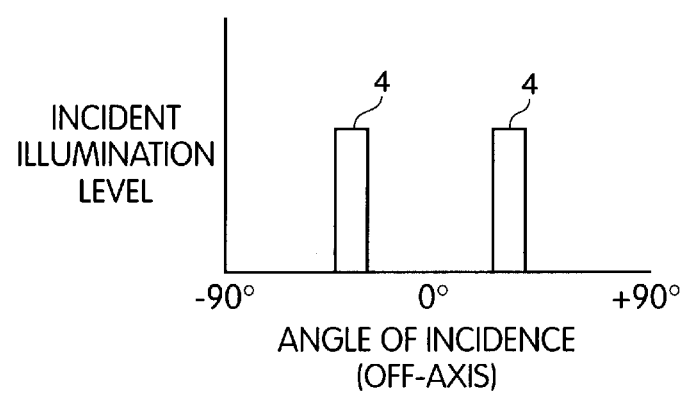
Figure 7:
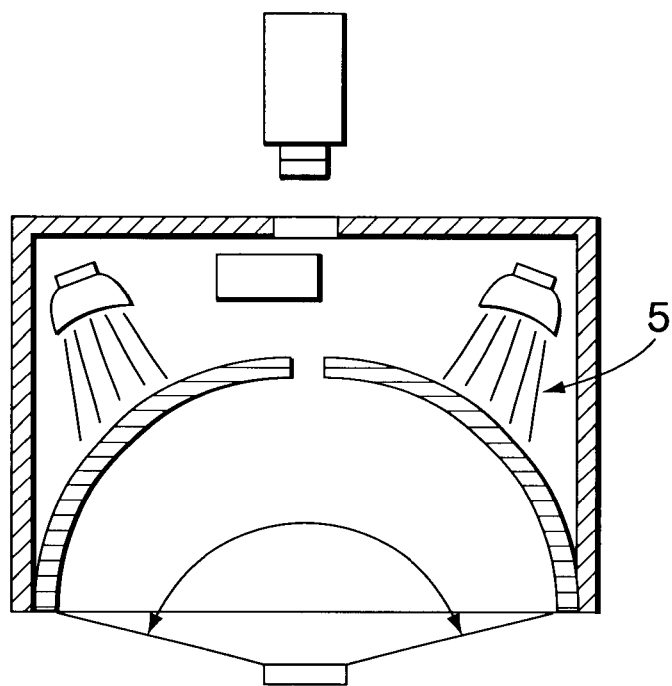
FIGS. 7 and 9 depict embodiments of continuous diffuse illumination geometries.
Figure 8:
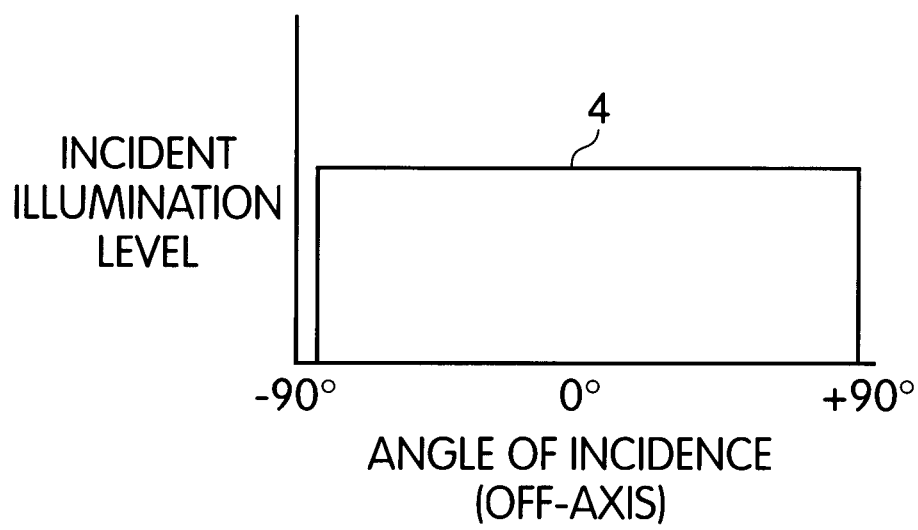
FIGS. 8 and 10 depict the incident angle brightness histograms associated with the lighting geometries depicted in FIGS. 7 and 9 respectively.
Figure 9:
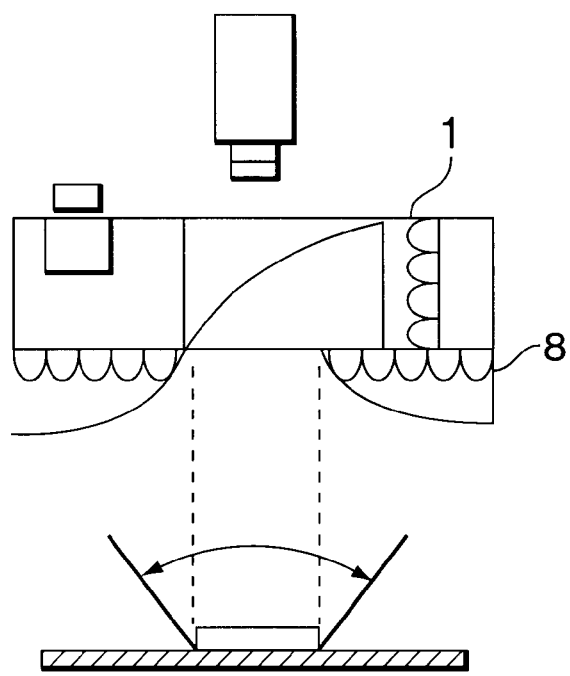
Figure 10:
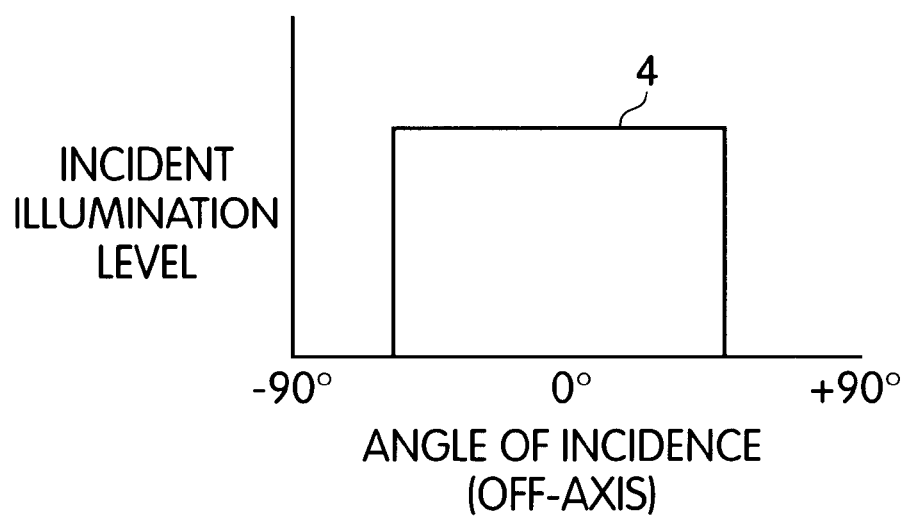
Figure 11:
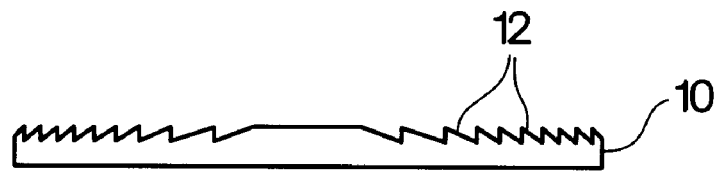
FIG. 11 depicts a side view of a conventional fresnel lens.
Figure 12:
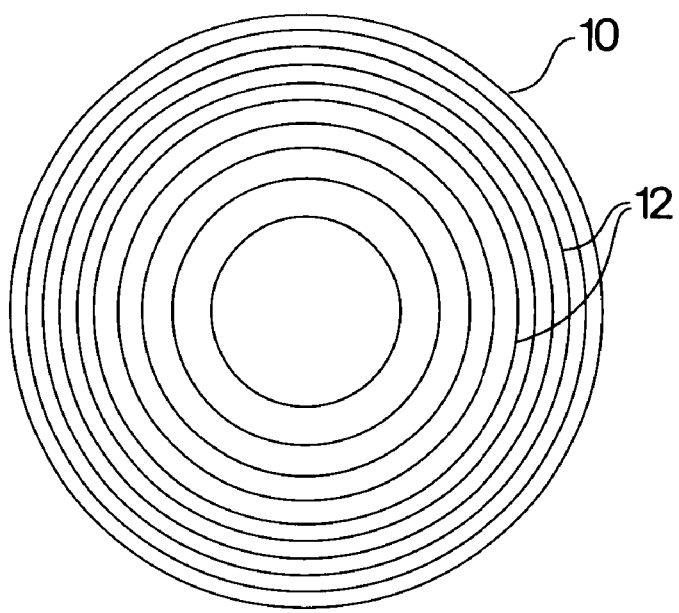
FIG. 12 depicts a front view of the fresnel lens of FIG. 11.
Figure 13:
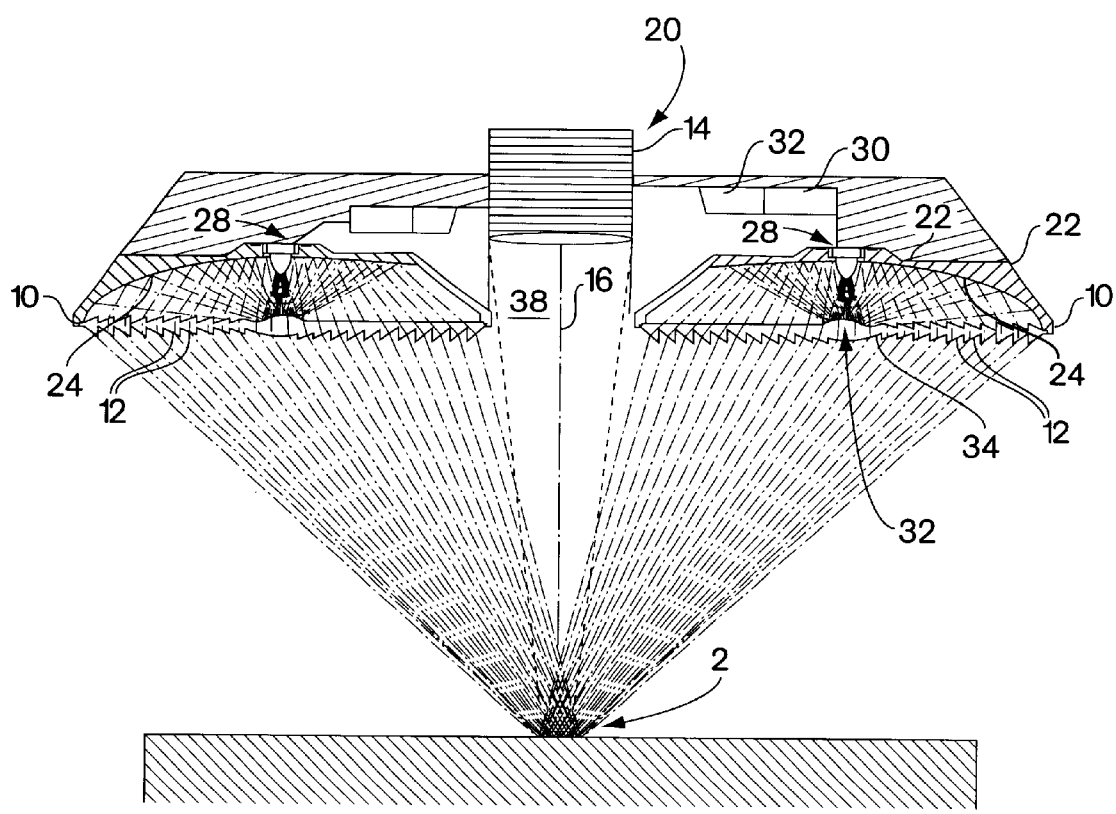
FIG. 13 depicts a side, cross-sectional view of an embodiment of a ring light of the present invention.

FIG. 13 depicts a side, cross-sectional view of components illustrating one embodiment of the inventive concepts, wherein the object 2 is to be observed under illumination by a device 20. In an embodiment of the invention, the object 2, which, in the practice of the invention, could include a shiny or specular surface, such as the soldered surfaces of a printed circuit board, or a laser etched metal surface, reflective packaging surface, or the like, a dull surface, such as copy paper, a flat surface, such as paper, or an irregular or non-flat configuration, may be viewed by a camera 14. The viewing of the object 2 may occur along the observation axis 16 as indicated in FIG. 13. It should be understood that the device 20 may be provided without the camera 14.

The purpose of viewing the object 2 by the camera 14 may be for any purpose requiring visual inspection, ranging from machine vision inspection, to reading of a matrix code, bar code or character string, to inspection for flaws. Observation may be for any desired reason, such as for purposes of orientation or assembly prior to subsequent machining operations, or reading or reproducing printed, inscribed or chemical- or laser- etched art work or print. Significant variations in the local intensity of light reflected from an uneven specular surface will result only from localized surface slope deviations from flatness greater than half the incident illumination angle with respect to the optical axis, such as are commonly associated with surface imperfections, and not from less severe normal deviations in surface geometry that are not associated with defect conditions.

In the embodiment of the invention depicted in FIG. 13, the device 20 includes a housing 22, which may be a molded plastic body or other housing capable of supporting the other elements of the invention described herein. The housing 22 may have an inner reflective surface 24. In an embodiment of the invention, the inner reflective surface 24 is a concave reflector cavity that reflects light off the concave surface along the general direction of the illumination axis 16 toward a surface on which the object 2 is disposed.

The device 20 may further include an illumination source 28, which may be disposed on the housing 22 in a ring on the inner reflective surface 24 of the housing 10. In an embodiment, the illumination source 28 is central to the inner reflective surface 24 and is disposed in a ring about the center of the device 20. The illumination source 28 may be a conventional illumination source, such as a ring light. In an embodiment, the illumination source 28 is a ring of light emitting diodes. The illumination source 28 may be controlled by a circuit 30, which is shown in block diagram format in FIG. 13, which may in turn be controlled by a processor 32, also shown in block diagram format. In an embodiment of the invention in which the illumination source is a ring of light emitting diodes, the diodes may be of different colors, and the processor 32 may control the color and intensity of the illumination coming from the illumination source 28 by controlling the individual diodes.

The device 20 may further include the fresnel lens 10 disposed on the housing 22 opposite the inner reflective surface 24, for focusing illumination reflected to from the inner reflective surface 24 to the object 2. The fresnel lens 10 may be constructed from an expensive, light transmitting material, such as acrylic. If the device 20 is held close enough to the object 2, light focused from the concentric grooves 12 of the fresnel lens 10 to the object 2 will arrive at a large solid angle of illumination, rendering continuous diffuse illumination conditions. That is, light will arrive from a variety of directions other than along the visual inspection axis 16. The pitch of the fresnel lens 10 may be made fine enough that discontinuities in the illumination field will be effectively out of focus when reflected off the object 2. The fresnel lens 10 may include an aperture 38 disposed about the illumination axis 16, which permits the camera 14 to view the object 2 along the illumination axis 16.

Figure 14:
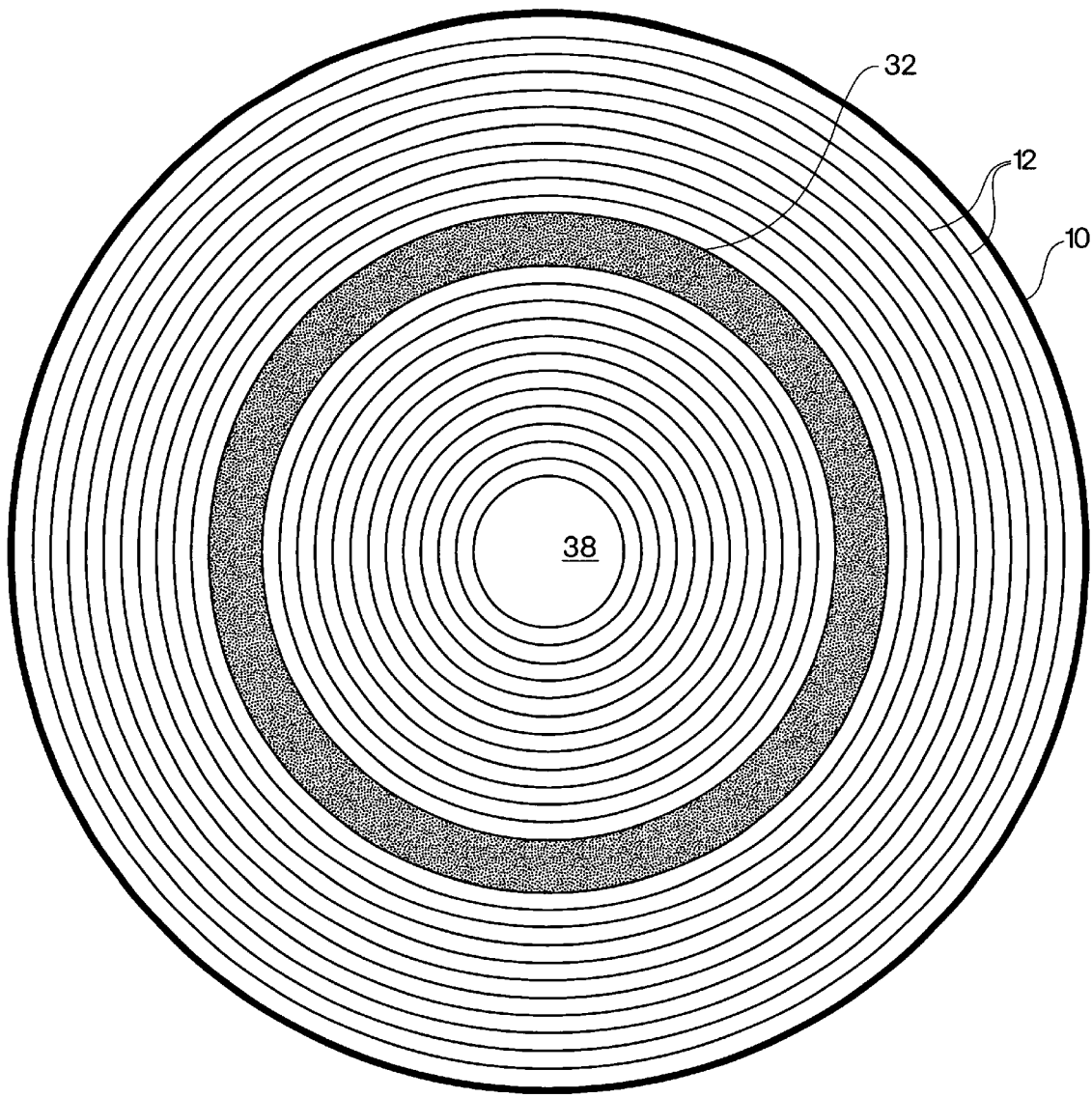
FIG. 14 depicts a bottom view of the embodiment of FIG. 13.

FIG. 14 depicts a bottom view of the device 20, in which the outer surface 34 of the fresnel lens 10 is seen. The fresnel lens 10 includes the aperture 38 and the concentric grooves 12.

Referring to FIGS. 13 and 14, the device 20 may include a partially reflective reflector 32. Referring to FIG. 13, in an embodiment, the partially reflective reflector 32 may be disposed on the fresnel lens 10 at a position opposite the illumination source 28. Referring to FIG. 14, the partially reflective reflector 32 may thus be disposed along a concentric ring about the aperture 38 of the fresnel lens 10, at a position approximately half of the distance of the radius of the fresnel lens 10 from the illumination axis 16. Referring again to FIG. 13, the partially reflective reflector 32 may be constructed to transmit part of the illumination from the illumination source 28 through the center of the fresnel lens 10 and to reflect another part of the illumination from the illumination source 28 back toward the inner reflective surface 24. The illumination reflected back to the inner reflective surface 24 may then be reflected back to the fresnel lens 10 for focusing on the object 2. Thus, the partially reflective reflector 32 scatters light from the point (in cross-section) or ring of the illumination source 28 at a wide range of angles onto the inner reflective surface 24, which further scatters the light onto the fresnel lens 10, permitting the fresnel lens 10 to produce a wide range of illumination angles of the object 2, while using a small source. The high efficiency of transmission characteristic of fresnel lenses permits use of a small, cool, efficient illumination source, such as a light emitting diode.

The partially reflective reflector 32 may be formed as a half-silvered, convex, inner surface of the fresnel lens 10. That is, a center portion of the fresnel lens 10 may be partially silvered, so that the center portion reflects a divergent light bundle back to the inner reflective surface 24, while transmitting some fight through to the object 2. The divergent fight bundle is then reflected back off the inner reflective surface 24 through the fresnel lens 10, to the object 2. The light that passes through the half-silvered partially reflective reflector 32 of the fresnel lens 10 emerges through a convex outer lens surface 34 of the center of the fresnel lens 10 and is focused on the object being observed. The density profile of the partially reflective reflector 32 may be designed to cause the transmitted fight to match in intensity the average intensity from the fresnel lens 10. The result is a large solid angle of incident illumination where a high percentage of the output of the LEDs is focused on the object being observed. In an embodiment, the device 20 may have an efficiency sufficient to permit the light to be effectively strobed.

The camera 14 may be a machine vision camera, for producing an image corresponding to the object. The device 20 may farther include the processor 32. The processor 32 may control the circuit 30 for controlling the illumination source 28. In an embodiment of the invention, the circuit 30 may be used to control white light emitting diodes to alter the intensity of the illumination from the device 20, either globally, or in discrete segments of the illumination source 28. If color light emitting diodes are used as the illumination source, then the circuit 30 may be used to control the color of light from the device 20. In embodiments, high intensity red light emitting diodes, or alternating red, green and blue light emitting diodes may be used.

The processor 32 may further process the image from the camera 14 to generate data. The processor 32 may be included in the housing 22, it may be an external processor 32, or the processor 32 may be understood to encompass one or more different processors located in the housing 22, external to the housing 22, or both. Part of the processor 32 may process the data from the camera 14. Thus, the processor 32 may be part of a system for storage, manipulation, or retrieval of image data, such as an inventory management system, a materials handling system, or a process control system. Thus, the data from the device 20 may be transmitted, via a connector, or by other transmission mechanisms, such as infrared, radio, or other mechanism, to an external computer or computers which may be part of other systems and apparatuses that are responsive to image data. Such systems can include process control systems, manufacturing systems, inventory management systems, material handling systems, robotic arms, or any other robotic or machine vision systems. Thus, the device 20 may be integrated into any other device that is responsive to imaging data. The device 20 may similarly be any device that includes an image processor, such as a hand held scanner, a matrix code reader, or a semiconductor manufacturing device.

Figure 15:
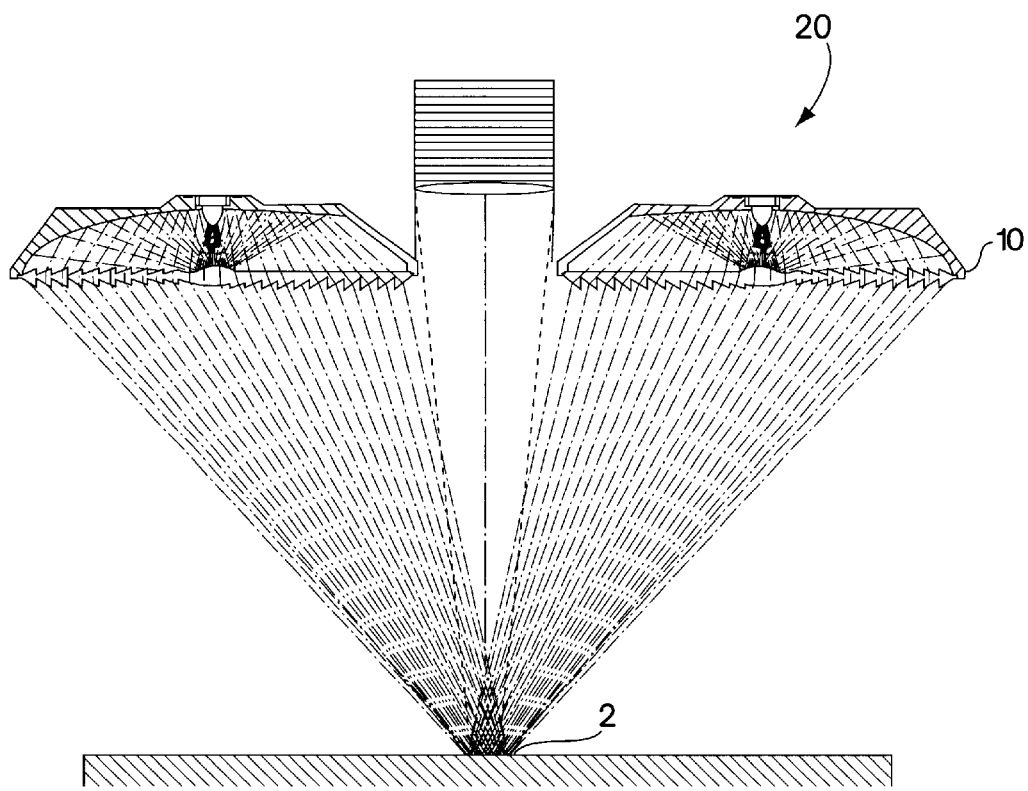
FIGS. 15 and 16 depicts side, cross-sectional views of embodiments having different focal lengths.
Figure 16:
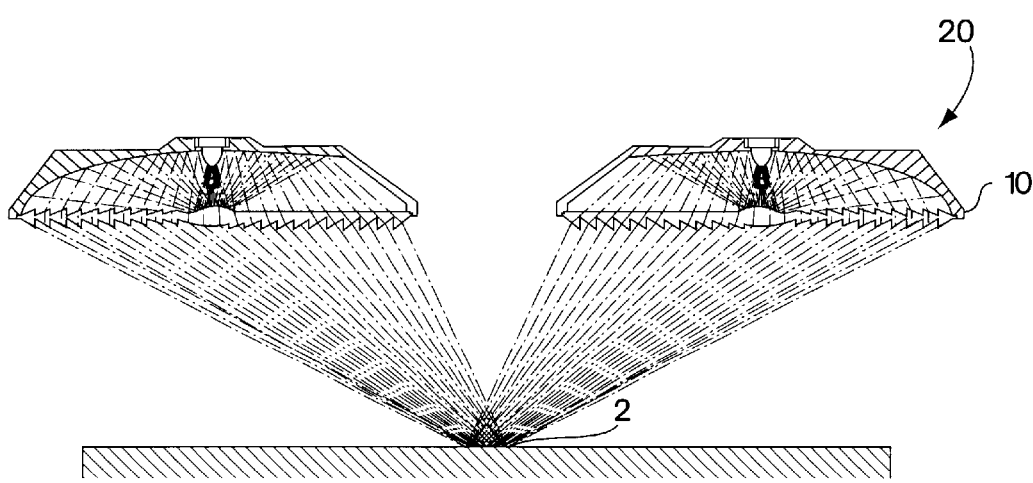

Since a fresnel lens 10 has a single focal length, satisfactory illumination conditions (continuous diffuse illumination conditions) will be produced by the device only in a particular range of distances from the device 20. Accordingly, referring to FIGS. 15 and 16, the fresnel lens 10 may be made removable, so that the fresnel lens 10 is interchangeable with another lens. Thus, as depicted in FIG. 15 and FIG. 16, the device 20 may be provided with different focal lengths of fresnel lens 10, meaning that the device 20 can be used to view an object 2 at different distances from the device 20 with a large solid angle of illumination. In an embodiment of the invention, a primary fresnel lens 10 provides a focal length sufficient to provide continuous diffuse illumination conditions if the device 20 is positioned about four inches from the object 2, and alternate lenses may be provided for different distances.

The housing 22 may be formed of molded plastic, with the fresnel lens 22 being made of acrylic. Thus, the device may be made extremely rugged, easy to assemble, easy to manufacture and easy to maintain. A ring of light emitting diodes, if used as the illumination source 28, would be easy to replace. A fan could be disposed on the housing 22 to cool the device 22, if desired.

Methods of image processing encompassed herein include providing a ring of light emitting diodes as the illumination source 28, reflecting light from the illumination source 28 with the partially reflective reflector 32 to the internal reflective surface 24 and focusing illumination reflected from the internal reflective surface 24 with the fresnel lens 10 to the object 2. Methods disclosed herein further include providing the camera 14 for producing an image of the object, and providing a processor for controlling the illumination source 28 and for storing, manipulating and retrieving data from the camera 14.

Since certain changes may be made in the above described illumination device, without departing from the spirit and scope of the invention herein involved, it is intended that all of the subject matter of the above description or shown in the accompanying drawings shall be interpreted merely as illustrative examples and shall not be construed as limiting the invention.

What is claimed is:

1. A device for illuminating an object, comprising:

a housing having an inner reflective surface;

an illumination source, disposed in a ring on the inner reflective surface;

a fresnel lens disposed on the housing opposite the inner reflective surface, for focusing illumination to the object; and a partially reflective reflector, disposed on the fresnel lens, for transmitting illumination to the object and for reflecting illumination to the inner reflective surface.

2. The device of claim 1, wherein the illumination source is a plurality of light emitting diodes.

3. The device of claim 1, wherein the illumination source is a ring light.

4. The device of claim 1, wherein the partially reflective reflector is a half-silvered mirror.

5. The device of claim 1, wherein the housing includes an aperture, further comprising:

a camera for viewing the object.

6. The device of claim 5, wherein the camera is a machine vision camera for producing an image corresponding to the object.

7. The device of claim 6, further comprising:

a processor, for processing the image to generate data.

8. The device of claim 7, further comprising:

an inventory management system for processing the data.

9. The device of claim 7, further comprising:

a materials handling system for processing the data.

10. The device of claim 7, further comprising:

a matrix code reader for processing the data.

11. The device of claim 7, further comprising:

a process control system for processing the data.

12. The device of claim 7, further comprising:

a hand held scanner for processing the data.

13. The device of claim 1, wherein the fresnel lens is removable, so that the fresnel lens is interchangeable with another lens.

14. The device of claim 1, further comprising:

a circuit for controlling at least one of the color and the intensity of the illumination source.

15. The device of claim 14, wherein the illumination source is a ring of light emitting diodes of a plurality of different colors.

16. The device of claim 1, further comprising:

a fan for cooling the device.

17. A method of image processing an image from an illuminated object, comprising:

providing a ring of light emitting diodes;

providing a partially reflective reflector;

providing a fresnel lens for focusing illumination on the object;

providing a camera for viewing the object;

providing a vision processor for processing data from the camera; and providing a computer for storing manipulating and retrieving data from the vision processor.

18. The method of claim 16, wherein the computer controls a process based on the data.

19. The method of claim 17, wherein the process is a manufacturing process.

20. The method of claim 17, wherein the process is an inventory control process.

21. The method of claim 17, wherein the process is a materials handling process.

22. A method of illuminating an object, comprising:

providing an illumination source;

providing a fresnel lens for focusing illumination on the object;

providing a partially reflective reflector, disposed on the fresnel lens, for transmitting illumination to the object and for reflecting illumination to the inner reflective surface; and providing a reflective surface, for reflecting illumination from the partially reflective reflector to the fresnel lens.

23. The method of claim 22, wherein the illumination source is a plurality of light emitting diodes.

24. The method of claim 22, wherein the illumination source is a ring light.

25. The method of claim 22, wherein the partially reflective reflector is a half-silvered mirror.

26. The method of claim 22, further comprising:

providing a camera for viewing the object.

27. The method of claim 26, wherein the camera is a machine vision camera for producing an image corresponding to the object.

28. The method of claim 27, further comprising:

processing the image to generate data.

29. The method of claim 28, further comprising:

providing an inventory management system for processing the data.

30. The method of claim 28, further comprising:
providing a materials handling system for processing the data.

31. The method of claim 28, further comprising:
providing a matrix code reader for processing the data.

32. The method of claim 28, further comprising:
providing a process control system for processing the data.

33. The method of claim 22, wherein the fresnel lens is removable, so that the fresnel lens is interchangeable with another lens.

34. The method of claim 22, further comprising:
controlling at least one of the color and the intensity of the illumination source.

* * * * *